United States Patent [19]

Aoyama

[11] Patent Number: 5,527,960
[45] Date of Patent: Jun. 18, 1996

[54] FLUORINATING REAGENTS AND METHOD OF FLUORINATION

[75] Inventor: Hirokazu Aoyama, Settsu, Japan

[73] Assignee: Daikin Industries Ltd., Osaka, Japan

[21] Appl. No.: 373,280

[22] PCT Filed: Jul. 19, 1993

[86] PCT No.: PCT/JP93/01014

§ 371 Date: Jan. 24, 1995

§ 102(e) Date: Jan. 24, 1995

[87] PCT Pub. No.: WO94/03414

PCT Pub. Date: Feb. 17, 1994

[30] Foreign Application Priority Data

Jul. 31, 1992 [JP] Japan ................................ 4-224591

[51] Int. Cl.$^6$ ........................................ C07F 9/02
[52] U.S. Cl. ............................. 564/12; 568/16
[58] Field of Search ..................... 568/16; 564/12

[56] References Cited

PUBLICATIONS

Chem Abst (CA) 93: 167763 1980.
CA 91: 123804 1979.
CA 111: 23589 1988.
CA 110: 192925 1988.
CA 105: 209036 1985.
CA 103: 105059 1985.

Primary Examiner—Paul J. Killos
Attorney, Agent, or Firm—Armstrong, Westerman, Hattori, McLeland & Naughton

[57] ABSTRACT

Fluorinating reagents expressed in a general formula;

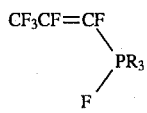

(In the general formula, R is an alkyl group having 1 to 5 carbons or a dialkylamino group in which each alkyl group has 1 to 3 carbons.), and a fluorinating method to fluorinate an alcoholic hydroxyl group by using the reagent. Raw materials of the aforesaid fluorinating reagents can be easily converted to object products and are less poisonous and corrosive. Their procurement and preparation are also easy. Further, it is easy to fluorinate compounds containing an alcoholic hydroxyl group by using this fluorinating reagents.

4 Claims, No Drawings

FLUORINATING REAGENTS AND METHOD OF FLUORINATION

This invention relates to fluorinating reagents needed for producing compounds containing fluorine which are important as medicines and their intermediates and to the method of fluorination which uses the fluorinating reagent.

PRIOR ART

As reagents and methods of fluorinating an alcoholic hydroxyl group, following methods shown in (1) to (5) have been known so far.

(1) A method of fluorinating a hydroxyl group in secondary alcohol or tertiary alcohol by using HF or HF/pyridine solution (M. Hudlioky, "Chemistry of Organic Fluorine Compounds", 2nd ed., Ellis Hotwood Ltd. 1976, page 689: G. A. Olah et al., Synthesis, 1973, page 786).

(2) A method in which after a hydroxyl group in alcohol is converted to an ester of sulfonio acid, the ester is fluorinated by making it react with alkalimetal fluoride including KF (M. Hudlicky, "Chemistry of Organic Fluorine Compounds", 2nd ed., Ellis Horwood Ltd. 1976, page 689).

(3) A method of fluorinating a hydroxyl group by using fluoroalkylamine as a fluorinating reagent which is obtained from the reaction of secondary amine with ohlorotrifluoroethylene or hexafluoropropene (E. D. Bergmann et al., Isr. J. Chem., Vol. 8, page 925, 1970: Ishikawa et al., "Chemistry of Organic Synthesis", Vol. 37, No.7, page 607, 1979).

(4) A method of fluorinating a hydroxyl group by using diethylamino sulfur trifluoride (DAST) as a fluorinating reagent (W. J. Middleton et al., "Org. Synthesis", Vol. 57, page 50, 1977).

(5) A method of fluorinating a hydroxyl group by using as a fluorinating reagent difluorotriphenyl-phosphorane from the reaction of triphenylphosphine with sulfur tetrafluoride (Kobayashi et al., "Chem. Pharm. Bull." (Tokyo), Vol. 16, page 1009, 1968).

The inventor of this invention studied new fluorinating reagents, especially those containing phosphorus, in place of the above-mentioned well-known fluorinating reagents.

It is not easy to prepare the fluorinating reagent described in the above (5), because very poisonous and corrosive sulfur tetra-fluoride must be used as a raw material.

OBJECTS OF THE INVENTION

The object of this invention is to offer fluorinating reagents containing phosphorus which can be easily and safely synthesized.

Another object of this invention is to offer a method of efficiently fluorinating an alcoholic hydroxyl group by using the fluorinating reagent containing phosphorus.

THE CONSTITUTION OF THE INVENTION

As a result of eagerly repeating searches and studies of the above-mentioned fluorinating reagents which contain phosphorus and are easy to prepare, the inventor found that fluoro-(1-pentafluoro-1-propenyl)-tributyl phosphorane (hereinafter abbreviated FPTBP) obtained from the reaction of hexafluoropropene (hereinafter abbreviated HFP) with tributyl phosphine (hereinafter abbreviated TBP) could be used as a fluorinating reagent to fluorinate an alcoholic hydroxyl group, having reached the success of completing this invention.

That is, this invention relates to fluorinating reagents (e.g. FPTBP) expressed in a general formula;

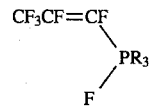

(In the general formula, R is an alkyl group having 1 to 5 carbons or a dialkyl-amino group in which each alkyl group has 1 to 3 carbons.)

This invention also offers a fluorinating method that is characteristic of substituting fluorine for the above-mentioned alcoholic hydroxyl group by the reaction of the fluorinating reagent and an organic compound containing an alcoholic hydroxyl group.

A fluorinating reagent in this invention, FPTBP, for example, is easily produced by the reaction of TBP and HFP in such a solvent as methylene ohioride, diethyl ether, and diethylene glycol dimethyl ether (See D. J. Burton et al., "J. Fluorine Chem." Vol 44 page 167, 1989).

In this case, several ways can be taken, such as a way in which HFP is blown into TBP dissolved in a solvent to make them react, a reaction under normal pressure in which HFP is put into after being condensated by cooling and is made react with TBP, and a way that after putting a solvent and TBP into an autoclave HFP is introduced under pressure to make it react with TBP.

When synthesis of fluorinating reagents is carried out with the method of this invention, besides the above-mentioned TBP, trialkylphosphines, including trimethylphosphine, triethylphosphine, and tripropylphosphine, or tris (dialkylamino) phosphines, including tris (dimethylamino) phosphine and tris (diethyl-amino) phosphine, can also be used.

Such various kinds of raw materials can be easily converted to object products and are less poisonous and corrosive. And they are easily prepared. Moreover, as TBP and its above-mentioned substitutes, and HFP are all easily available, those materials being on sale can be used as they are.

By using one of the aforementioned phosphines, a fluorinating reagent, its R in the above-mentioned general formula is corresponding to that of the used phosphine, can be obtained.

A compound containing an alcoholic hydroxyl group to be fluorinated is added in a fluorinating reagent such as FPTBP solution obtained in this way.

The mixture is kept at the reaction temperature of −10°–100° C., preferablly at 0°–80° C. and stirred, then a compound with substituted fluorine for its hydroxyl group and 1,1,1,2,3-pentafluoropropene are produced. The products can be separated from the reaction mixture by distillation under normal or reduced pressure. The amount of FPTBP is preferable to be more than the equivalent to a hydroxyl group to be fluorinated.

As compounds having an alcoholic hydroxyl group which can be fluorinated by using fluorinating reagents in this invention, though they are not particularly limited, alcohols such as methanol, ethanol, propanol, isopropanol and octyl alcohol, and compounds having asteroid structure with a hydroxyl group (various compounds except those having OH group of oarboxylic acid) are considered.

THE POSSIBILITY OF UTILIZING THE INVENTION IN INDUSTRY

Since fluorinating reagents in this invention are those compounds expressed in the above-mentioned general formula, raw materials of the reagents can be easily converted to object products and are less poisonous and corrosive. Their procurement and preparation are also easy. Further, it is easy to fluorinate compounds containing an alcoholic hydroxyl group by using this fluorinating reagents.

EXAMPLE

The invention will be explained in detail in the following examples.

EXAMPLE 1

Twenty ml of diethyleneglycol dimethyl ether and 20.3 g of TBP were put in a 100 ml glass reaction vessel equipped with a gas introduction tube and a condenser cooled by dry ice. With the mixture cooled at 5°–10° C., HFP was introduced through the gas introduction tube. HFP introduction rate was controlled so that inner temperature didn't rise over 10° C. After 15 g of HFP had been introduced, the mixture was further stirred for 1 hour at 5°–10° C.

Then, after replacing the gas introduction tube with a dropping funnel, 4.6 g of ethyl alcohol was dropped while keeping the reaction temperature at 5°–10° C. After the end of dropping, the reaction mixture was returned to room temperature and stirred continuously. In the first place, 1,1,1,2,3-pentafluoropropene was produced. Then, monofluoroethane began to be produced when the reaction mixture was heated to 50°–55° C. and continuously stirred. After 5 hrs. heating and stirring, products were collected in a cold trap cooled at −70° C. The weight of the collected liquid was 17.5 g. Gas ohromatographio analysis showed that the liquid was composed of 74.3 wt % of 1,1,1,2,3-pentafluoropropene and 25.7 wt % of monofluoroethane. According to the result, the yield of monofluoroethane was 94%.

Furthermore, a fluorinating reagent FPTBP produced by the above-mentioned reaction of TBP and HFP; fluoro-(1-pentafluoro-1-propenyl)-tributyl phosphorane was identified by $^{19}$F-NMR and $^{31}$P-NMR analysis. Monofluoroethane produced in the fluorinating reaction was also identified by $^{19}$F-NMR and $^1$H-NMR analysis, and by Mass analysis. All the analysis data showed the same values as those reported in literatures.

EXAMPLE 2

Instead of ethanol, 6 g of isopropanol was used in the same reaction as Example 1. As the result, the amount of the collected liquid was 17.2 g. Gas chromatographic analysis showed that the liquid was composed of 69.2 wt % of 1,1,1,2,3-pentafluoropropene and 30.8 wt % of 2-fluoropropane. According to the result, the yield of 2fluoropropane was 85%.

I claim:

1. A method for replacing a hydroxyl group in an alcohol by fluorine which comprises reacting the alcohol with a compound of the formula

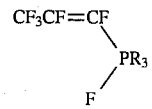

wherein R is a $C_{1-5}$ alkyl group or a di-$C_{1-3}$ alkylamino group.

2. A method according to claim 1, wherein R is a $C_{1-5}$ alkyl group.

3. A method according to claim 1, wherein R is a di-$C_{1-3}$ alkylamino group.

4. A compound of the formula

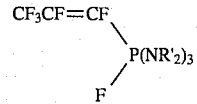

wherein each R' is a $C_{1-3}$ alkyl group.

* * * * *